(12) United States Patent
Jiang

(10) Patent No.: US 10,758,516 B2
(45) Date of Patent: Sep. 1, 2020

(54) METHODS AND COMPOSITIONS FOR THE TREATMENT OF GLIOMAS

(71) Applicant: University of Cincinnati, Cincinnati, OH (US)

(72) Inventor: Jianxiong Jiang, Blue Ash, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 16/108,121

(22) Filed: Aug. 22, 2018

(65) Prior Publication Data

US 2019/0060276 A1 Feb. 28, 2019

Related U.S. Application Data

(60) Provisional application No. 62/548,441, filed on Aug. 22, 2017.

(51) Int. Cl.
| | | |
|---|---|---|
| *A61K 31/4045* | (2006.01) | |
| *A61K 9/00* | (2006.01) | |
| *A61P 35/00* | (2006.01) | |

(52) U.S. Cl.
CPC ........ *A61K 31/4045* (2013.01); *A61K 9/0053* (2013.01); *A61P 35/00* (2018.01)

(58) Field of Classification Search
CPC .... A61K 31/4045; A61K 9/0053; A61P 35/00
USPC ...................................................... 514/419
See application file for complete search history.

(56) References Cited

U.S. PATENT DOCUMENTS

| 9,518,044 B2 | 12/2016 | Jiang et al. | |
| 2017/0042905 A1* | 2/2017 | Ganesh | A61K 45/06 |

FOREIGN PATENT DOCUMENTS

| WO | WO-2015167825 A1 * | 11/2015 | A61K 45/06 |

OTHER PUBLICATIONS

Grobben et al., Cell Tissue Res. (2002), v.310, p. 257-270.*
Oliver et al., Translational Cancer Research, (2016), 5(Suppl 6), S1073-1077.*
Sung-Hee Chang et al, "The Prostaglandin E2 Receptor EP2 is Required for Cyclooxygenase 2-Mediated Mammary Hyperplasia"; Cancer Res 2005; 65:(11), 4496-4499.
Kyung-Soo Chun et al, "The Prostaglandin E2 Receptor, EP2, Regulates Survivin Expressoin Via an EGFR/STAT3 Pathway in UVB-Exposed Mouse Skin"; Molecular Carinogenesis 50:439-448 (2011).
Jianxiong Jiang and Ray Dingledine, "Prostaglandin receptor EP2 in the crosshairs of anti-inflammation, anti-cancer, and neuroprotection"; Trends Pharmacol Sci., Jul. 2013; 34(7): 413-423.
Jianxiong Jiang and Ray Dingledine, "Role of Prostaglandin receptor EP2 in the Regulations of Cancer Cell Proliferation, Invasion, and Inflammation"; J Pharmacol Exp Ther 344:360-367, Feb. 2013.
Jianxiong Jiang et al, "Small molecule antagonist reveals seizure-induced mediation of neuronal injury by prostaglandin E2 receptor subtype EP2"; PNAS, Feb. 21, 2012, vol. 109, No. 8, 3149-3154.
Jianxiong Jiang et al, "Prostaglandin E2 Signaling: Alternative Target for Glioblastoma?"; Trends Cancer: Feb. 2017; 3(2): 75-78.
Xinrong Ma et al, "Frondoside A inhibits breast cancer metastasis and antagonizes prostaglandin E receptors EP4 and EP2"; Breast Cancer Res Treat Apr. 2012; 132(3): 1001-1008.
Antonio Omuro and Lisa M. Deangelis, "Glioblastoma and Other Malignant Gliomas"; JAMA, 2013; 310(17): 1842-1850.
Quinn T. Ostrom et al, "CBTRUS Statistical Report: Primary Brain and Central Nervous System Tumors Diagnosed in the United States in 2006-2010"; Neuro-Oncology 15: ii1-ii56, 2013.
Troy Payner et al, "Microsomal prostaglandin E synthase-1 regulates human glioma cell growth via prostaglandin E2-dependent activation of type II protein kinase A"; Mol Cancer Ther; 5(7); Jul. 2006.
Jiange Qiu et al, "Cyclooxygenase-2 in glioblastoma multiforme"; Drug Discov Today, Jan. 2017; 22(1): 148-156.
J. E. Rundhaug et al, "The role of the EP receptors for prostaglandin E2 in skin and skin cancer"; Cancer Metastasis Rev (2011) 30: 465-480.
Hiroshi Seno et al, "Cyclooxygenase 2- and Prostaglandin E2 Receptor EP2-dependent Angiogenesis in APCΔ716 Mouse Intestinal Polyps"; Cancer Research 62, 506-511, Jan. 15, 2002.
Masahiro Sonoshita et al, "Acceleration of intestinal polyposis through prostaglandin receptor EP2 in APCΔ716 knockout mice"; Nature Medicine, vol. 7, No. 9, Sep. 2001, 1048-1051.
James A. Sowers et al, "The Role of Inflammation in Brain Cancer," Chapter 4, Inflammation and Cancer, Advances in Experimental Medicine and Biology 816, 2014.
You Me Sung et al, "Lack of Expression of the EP2 but not EP3 Receptor for Prostaglandin E2 Results in Suppression of Skin Tumor Development"; Cancer Res 2005; 65: (20); Oct. 15, 2005, 9304-9311.
Maozhen Tian and William P. Schiemann, "PGE2 receptor EP2 mediates the antagonistic effect of COX-2 on TGF-β signaling during mammary tumorigenesis"; FASEB J. Apr. 2010; 24(4): 1105-1116.
Dingzhi Wang and Raymond N. Dubois, "Eicosanoids and cancer"; Nat Rev Cancer, Mar. 2010; 10(3): 181-193.
Kaiming Xu et al, "COX-2 overexpression increases malignant potential of human glioma cells thorugh Id1"; Oncotarget, vol. 5, No. 5, 2013, 1241-1252.

* cited by examiner

*Primary Examiner* — Yong L Chu
(74) *Attorney, Agent, or Firm* — Dinsmore & Shohl LLP

(57) ABSTRACT

Pharmaceutical compositions of selective EP2 antagonists exemplified by small molecules TG4-155 and TG6-10-1 effective for treating gliomas, and methods for administering the pharmaceutical compositions to treat subjects suffering from disorders characterized by gliomagenesis.

8 Claims, 8 Drawing Sheets

METHODS AND COMPOSITIONS FOR THE TREATMENT OF GLIOMAS

CROSS REFERENCE TO RELATED APPLICATION

This application claims benefit under 35 U.S.C. § 119(e) to U.S. Provisional Application No. 62/548,441 filed on Aug. 22, 2017, the entire disclosure of which is incorporated herein by this reference.

GOVERNMENT INTERESTS

This invention was made with government support under grants No. R01NS100947 and R00NS082379 awarded by The National Institutes of Health. The Government has certain rights in the invention.

BACKGROUND

With 17,000 new cases diagnosed each year in the U.S. or an annual incidence of 5.3/100,000 population, malignant gliomas account for about 80% of all primary malignant brain tumors, and 82% of these cases are classified as the WHO grade IV tumor—glioblastoma multiform (GBM) (Ostrom et al, 2013). The median survival time of GBM patients from diagnosis with treatment is only about 15 months. Without treatment, most GMB patients survive for only a few months (Sowers et al, 2014). Malignant gliomas are characterized by rapid growth and diffuse aggressive invasion within the brain, leading to a variety of debilitating neurological and psychiatric symptoms, such as nausea and vomiting, aphasia, hemispatial neglect, visual field defect, cognition changes, gait imbalance, urinary incontinence, blurred vision, headache, memory loss, hemiparesis, and personality changes.

Due to the restriction of infiltration by the blood-brain barrier of most anti-tumor drugs into the central nervous system (CNS), the standard treatment for malignant gliomas is limited to surgical resection followed by conventional radiotherapy in combination with temozolomide (Bernardi et al, 2009). However, the overall outcome of surgical treatment for gliomas is often compromised by the complexity of intracranial operation, extent of resection, and residual tumor cells that can cause tumor recurrence with a relatively short relapse time. Moreover, there are many cases where surgical ablation is not an option due to tumor location, tumor size and/or poor patient performance status. In addition, glioma cells, especially those in recurrent glioblastomas, have proven to be extremely resistant to conventional chemotherapy and radiotherapy. All these unfortunate factors together make gliomas the most difficult to treat as well as the most lethal of the malignant brain tumors. Developing new therapeutics for this devastating neurological condition is an urgent and unmet need.

Although the molecular mechanisms underlying gliomagenesis are poorly understood, growing evidence from studies on animal models and human patients suggests that cyclooxygenase-2 (COX-2) might be involved in the development of gliomas (Xu et al, 2014; Qiu et al, 2017). COX-2 is commonly overexpressed in gliomas, and its expression level is highly positively correlated with the tumor grade. As a major enzymatic product of COX-2, prostaglandin E2 ($PGE_2$) mediates inflammatory processes within the brain and facilitates the progression of many chronic inflammation-associated neurological diseases via its four downstream receptors—EP1, EP2, EP3, and EP4. EP1 receptor is a $G\alpha_q$-coupled to mediate the mobilization f cytosolic $Ca^{2+}$ and activation of protein kinase C (PKC); EP2 and EP4 are linked to $G\alpha_s$ that activiates adenylyl cyclase, resulting in the synthesis of cAMP (Jiang and Dingledine, 2013a). $PGE_2$ has been proposed to cause tumorigenesis through all four EP receipts (Payner et al, 2006; Wang and Dubois, 2010; Jiang and Dingledine, 2013a). The present investigators, as well as others, previously demonstrated that $PGE_2$ via EP2 promotes tumor cell survival, proliferation, angiogenesis and inflammation in several types of tumors including, for example, those in the colon, skin, breast, and prostate. However, to date, the identity of the EP receptor that directly mediates the development and progression of gliomas has been unknown. Identification of the EP receptor is critical for developing appropriately targeted therapeutics for this devastating disease.

SUMMARY

Accordingly, based on the surprising discovery by the present inventors that $PGE_2$-promoted cAMP synthesis in malignant glioma cells was largely blocked by selective EP2 antagonists, embodiments of the invention provide pharmaceutical compositions of selective small-molecule antagonists and methods for the treatment of patients suffering from a glioma.

One embodiment is directed do methods of treating a subject suffering from a disorder characterized by gliomagenesis, the methods comprising administering a pharmaceutical composition comprising at least one modulator of downstream Prostaglandin E2 (PGE2) signaling.

Another embodiment is directed to methods of treating a subject suffering from a disorder characterized by gliomagenesis, the methods comprising administering a pharmaceutical composition comprising a selective EP2 antagonist, "selective" defined herein as antagonizing EP2 by at least one order of magnitude greater than EP1, EP3 and/or EP4.

Other embodiments provide pharmaceutical compositions effective in treating malignant glioma. The compositions comprise at least one selective EP2 antagonist, and at least one pharmaceutically acceptable carrier, excipient, diluent, optionally an adjuvant, and optionally one or more further pharmaceutically active compounds.

Further embodiments are directed to methods for treating a subject at high risk for developing a glioma to reduce the risk of developing a glioma, the methods comprising administering a prophylactic regimen of a selective E2 antagonist.

These and other embodiments will be further detailed and clarified by reference to the Figures and detailed description, below.

Figures are provided to illustrate specific embodiments, aspects or features of the invention and should not be construed as limiting the full scope of the invention as provided by the appended claims.

DETAILED DESCRIPTION

Figure 1:
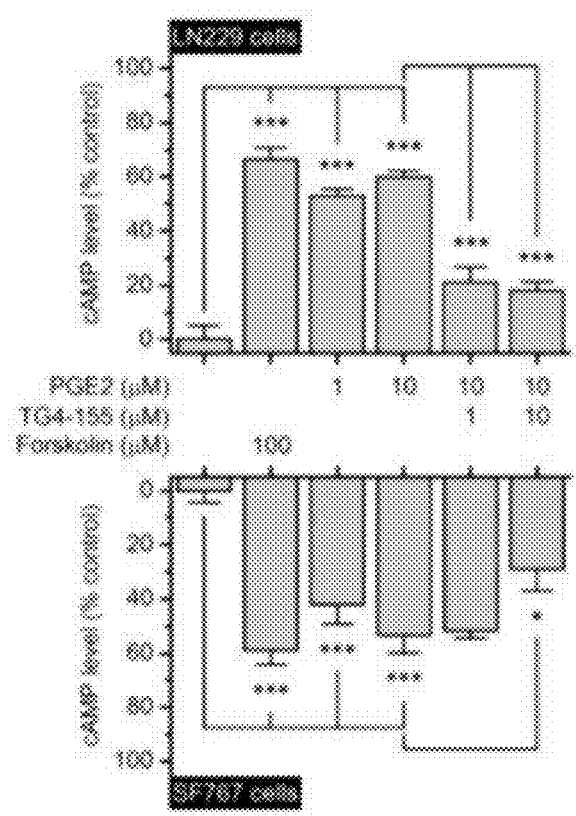
FIG. 1. Bar graph showing PGE2 mediated cAMP signaling via EP2 receptor in human malignant glioma cells LN229 (top) and SF767 (bottom).

The commonly induced COX-2 in glioma cells and tissues is well known for its role in tumorigenesis and COX-2 inhibition has been proposed and investigated as a therapeutic strategy for malignant brain tumors. However, using COX-2 selective and/or nonselective inhibitors to treat malignant gliomas has been discouraging due to recent inconsistent outcomes from a number of population studies and the early termination of several clinical trials. In addition, the past decade has also witnessed a growing recognition of the adverse effects of COX-2 inhibition on the microvessel systems, leading to the withdrawal of two legendary COX-2 inhibitor drugs—VIOXX® (rofecoxib) and BEXTRA® (valdecoxib) from the U.S. market. As such, it has been postulated by the present investigators and others that modulating downstream $PGE_2$ signaling might provide more therapeutic specificities than simply blocking the entire COX-2 cascade. Findings by the present investigators demonstrate that EP2 receptors provide a novel molecular target for the treatment/management of gliomas. In particular, pharmacological inhibition by small molecule antagonists exemplified by TG4-155 and TG6-10-1 provides an efficacious therapeutic strategy for the treatment of malignant brain tumors.

Taken together, these results demonstrate that the EP2 receptor is a dominant Gαs-coupled receptor that regulates COX-2/$PGE_2$-mediated cAMP signal pathways in human malignant glioma cells and is largely involved in inflammation, proliferation, migration and invasion of these brain tumor cells both in vitro and in vivo. $PGE_2$ signaling via EP2 receptor is therefore a major contributor to the development of malignant gliomas.

One embodiment provides methods of treating a subject suffering from a disorder characterized by gliomagenesis, the method comprising administering a pharmaceutical composition comprising a selective EP2 antagonist, "selective" defined herein as antagonizing EP2 by at least one order of magnitude greater than EP1, EP3 and/or EP4. Gliomas constitute a diverse group of primary (and to a lesser extent secondary) brain tumors that include those that are diffusely infiltrative and others that are well-circumscribed and low grade. Diffuse gliomas are classified by the World Health Organization as astrocytomas, oligodendrogliomas, or oligoastrocytomas and range in grade from II to IV. Glioblastoma (GBM) is the highest grade and most common form of astrocytoma. In the past, the diagnosis and grading of gliomas was based nearly entirely on histopathologic analysis. More recently an improved understanding of the role of genetics has led to changes in the standards for classification, prognostication, and predicting therapy response. For example, infiltrating astrocytomas and secondary GBMs are characterized by IDH, TP53, and ATRX mutations, whereas oligodendrogliomas demonstrate 1p/19q codeletion and mutations in IDH, CIC, FUBP1, and the telomerase reverse transcriptase (TERT) promoter. Primary GBMs typically lack IDH mutations and are instead characterized by EGFR, PTEN, TP53, PDGFRA, NF1, and CDKN2A/B alterations and TERT promoter mutations. Pediatric GBMs differ from those in adults and frequently have mutations in H3F3A, ATRX, and DAXX, but not IDH. In contrast, circumscribed, low-grade gliomas of childhood, such as pilocytic astrocytoma, pleomorphic xanthoastrocytoma, and ganglioglioma, often harbor mutations or activating gene rearrangements in BRAF. Neuropathologic assessment of gliomas increasingly relies on genetic testing for proper classification and patient management. According to specific embodiments, the subject suffers from malignant glioma, which may be primary, secondary, and which may be original or recurrent.

According to more specific embodiments, the subject suffers from glioma selected from grade II-IV astrocytoma, oligodendroglioma and oligoastrocytoma, and according to even more specific embodiments, the glioma comprises a grade IV astrocytoma selected from primary and secondary glioblastoma (GB). The subject is any animal with a central nervous system (CNS) subject to the development of a glioma (gliomagenesis). In specific embodiments, the subject is mammal, and in very specific embodiments the subject is a human.

Prostaglandin $E_2$ ($PGE_2$), a dominant enzymatic product of COX-2 in the CNS, is known to activate four G protein-coupled receptors: EP1, EP2, EP3 and EP4. When activated by $PGE_2$, EP2 stimulates adenylate cyclase (AC) resulting in elevation of cytoplasmic cyclic AMP (cAMP) concentration, which triggers multiple downstream events mediated by protein kinase A (PKA) and exchange protein activated by cAMP (Epac). Compounds that antagonize EP2 block or substantially block the cAMP cascade implicated in gliomagenesis. Efficacious selective EP2 antagonists are known in the art. "Selective" herein means having a greater than one order of magnitude binding affinity for EP2 over EP1, EP3 and EP4. Suitable small molecule EP2 antagonists and their pharmaceutically acceptable salts are disclosed in U.S. Pat. No. 9,518,044, the entire disclosure of which is incorporated herein by reference.

Figure 6:
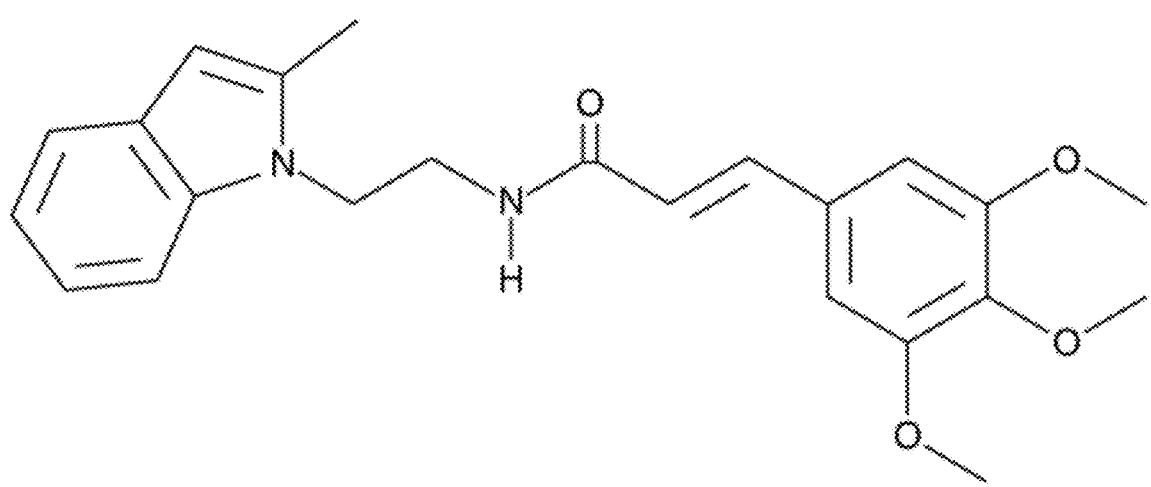
FIG. 6. Structural depiction of small molecule TG4-155.

According to very specific embodiments, the selective EP2 antagonist is selected from TG4-155, TG6-10-1, and combinations thereof. The structure of TG4-155 is set forth as FIG. 6, and the structure of TG6-10-1 is set forth as FIG. 7.

Methods of treating a subject suffering from a disorder characterized by gliomagenesis are also provided. Embodiments of the methods comprise administering a pharmaceutical composition comprising at least one modulator of downstream Prostaglandin E2 (PGE2) signaling. According to some specific embodiments, the downstream PE2 signaling comprises PGE2-mediated cAMP signaling. According to some specific embodiments, the modulator comprises a specific EP2 antagonist. Suitable antagonists are disclosed in U.S. Pat. No. 9,518,044. According to very specific embodiments, the EP2 antagonist is selected from TG4-155, TG6-10-1, and combinations thereof.

The pharmaceutical compositions of the invention may be formulated for administration by a variety of routes including the oral, rectal, transdermal, subcutaneous, intravenous, intramuscular, intranasal, or infusive routes, depending mainly on the specific formulation, the status of the subject, and the preference of the clinician. Targeted delivery formulations are also contemplated whereby the active agents are associated with a particle that is functionalized to be selective for cancer cells.

The pharmaceutical compositions of invention are formulated to deliver an "effective amount" of active agent upon administration to the subject, by which is meant any amount of an active that, upon suitable administration, is sufficient to achieve the desired therapeutic or prophylactic effect in the subject to which it is administered. The "effective amount" for any particular patient is influenced by age, size, gender, general health status, and cancer history and is determinable by a clinician with respect to a given presenting patient, and thus ranges are provided that reflect inherent flexibility.

Usually, depending on the condition to be prevented or treated and the desired route of administration, an effective amount of an EP2 antagonist will be between 0.01 to 1000 mg per kilogram body weight of the subject per day, more often between 0.1 and 500 mg, such as between 1 and 250 mg, for example about 5, 10, 20, 50, 100, 150, 200 or 250 mg, per kilogram body weight of the subject per day, which may be administered as a single daily dose, or divided over one or more daily doses. The amount(s) to be administered, the route of administration and any further treatment regimen may be determined by the treating clinician, depending, for example, on factors such as the age, gender and general condition of the subject and the nature and severity of the disease/symptoms to be treated. Stereoisomers of the compounds of the compositions, and tautomers of the compounds of compositions, are also contemplated as within the scope of the invention, and are generally included as within a broad recitation of a compound.

According to specific embodiments, administering comprises administering a dose of between 0.01 and 1000 mg/kg, between 0.1 and 500 mg/kg, between 1 and 250 mg/kg body weight, or 5, 10, 20, 50, 100, 150, 200 or 250 mg/kg body weight of the subject per day in one or multiple doses.

Another embodiment provides pharmaceutical compositions for use in treating gliomas, and in particular for treating a subject suffering from malignant glioma. The compositions comprise one or more selective EP2 antagonists, and at least one pharmaceutically acceptable carrier, and, optionally, one or more further pharmaceutically active compounds. Formulations containing one or more of the EP2 antagonists described herein may be prepared using a pharmaceutically acceptable carrier composed of materials that are considered safe and effective and may be administered to an individual without causing undesirable biological side effects or unwanted interactions. The "carrier", as utilized herein, includes all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions, including all components of a coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (N.Y., Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995), which provide information on carriers, materials, equipment and process for preparing tablets and capsules and delayed release dosage forms of tablets, capsules, and granules. The entire disclosures of these references are incorporated herein.

According to specific embodiments of the invention, "selective" is defined as antagonizing EP2 by at least one order of magnitude greater than EP1, EP3 and/or EP4. According to very specific embodiments, the selective EP2 antagonist is selected from TG4-155, TG6-10-1, salts, isomers, stereoisomers, and tautomer of TG4-155 and TG6-10-1, and combinations thereof.

Another embodiment is directed to methods for treating patients at high risk for developing a glioma to reduce the risk of developing a glioma, the methods comprising administering a prophylactic regimen of a selective E2 antagonist across a prophylactic time frame. "High risk" may include patients at risk of relapse after a period of remission after diagnosis and treatment of a glioma. "High risk" may include patients exhibiting a particular genetic profile and/or with one or more primary relatives with a history of diagnosis with glioma. In very specific embodiments, the patient is a pediatric patient. A prophylactic regimen comprises smaller dosing across longer time frames, for example across 30 days, 6 months, 1 year, 2 years or up to 5 years inclusive, with intermittent lag times of zero treatment that may last for any number of days, weeks or years. A prophylactic regimen is highly individualized and closely monitored.

According to some embodiments, the pharmaceutical compositions are formulated as unit dosage forms. Generally, such unit dosages comprise between 1 and 1000 mg, or between 5 and 500 mg, of an antagonist or combination of antagonists, for example, about 10, 25, 50, 100, 200, 300 or 400 mg per unit dosage. In specific embodiments, the unit dosage form comprises an oral dosage form. According to more specific embodiments, the oral dosage formulation comprises a delayed, extended, or pulsatile release formulation.

Compositions comprising extended, delayed and pulsatile dose forms are contemplated as within the scope of the invention and formulation is within the ordinary skill level in the art. As utilized herein, pulsatile dosing means that after a single administration, multiple drug doses are released at spaced apart intervals of time. Generally, upon ingestion of the dosage form, release of the initial dose is substantially immediate, i.e., the first release "pulse" occurs within about one hour of ingestion. This initial pulse is followed by a lag time during which very little or no drug is released from the dosage form, after which a second dose is then released. Similarly, a second lag time between the second and third release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses. According to very specific embodiments, pulsatile release dosing comprises closed and sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

The following Examples set forth data summaries of empirical work undertaken that forms the basis of the claimed invention. The Examples illustrate underpinning scientific concepts and specific embodiments and aspects and should not be construed as limiting the full scope of the invention as defined by the appended claims.

EXAMPLES

Example 1

Figure 7:
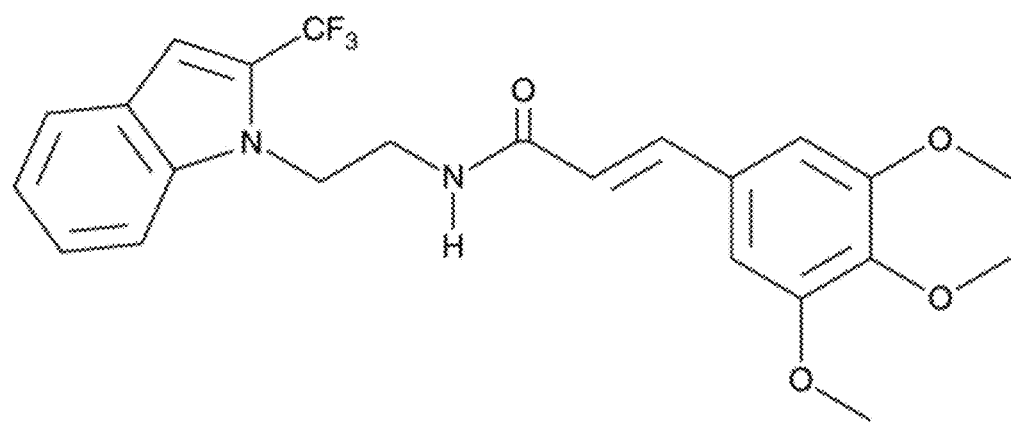
FIG. 7. Structural depiction of small molecule TG6-10-1.

Recently the present investigators demonstrated that $PGE_2$ increases cAMP levels in both human GBM cells LN229 and SF767 in a concentration-dependent manner, and this is replicated by forskolin—a direct activator of adenylate cyclase. The data set forth in FIG. 1 interestingly and surprisingly shows that the $PGE_2$-promoted cAMP synthesis in these malignant glioma cells was largely blocked by selective EP2 antagonists TG4-155 (FIG. 6) and TG6-10-1 (FIG. 7). FIG. 1 shows PGE2 mediated cAMP signaling via EP2 receptor in human malignant glioma cells LN229 (top) and SF767 (bottom), in the presence of 100 µM forskolin, 1 µM and 10 µM TG4-155 and 1 µM and 10 µM TG6-10-1. (n=5, *P<0.05; ***P<0.001, one-way ANOVA and post-hoc Bonferroni test). Data are shown as mean+SEM.

Example 2

Figure 2:
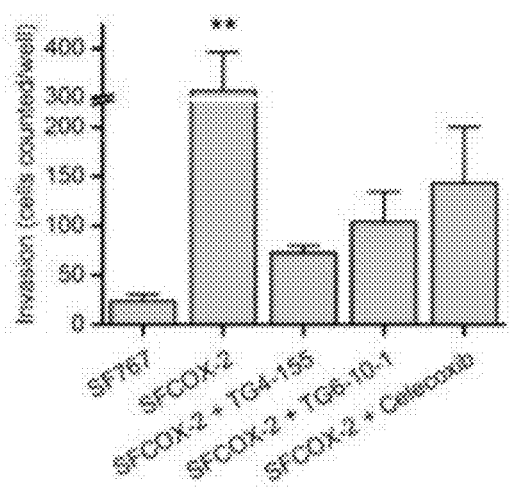
FIG. 2. Bar graph showing that overexpression of COX-2 in human GBM cells SF767 increased cell invasion, which was attenuated by EP2 antagonists—TG4-155 (10 µM), TG6-10-1 (10 µM), or COX-2 inhibitor celecoxib (10 µM).
Figure 3:
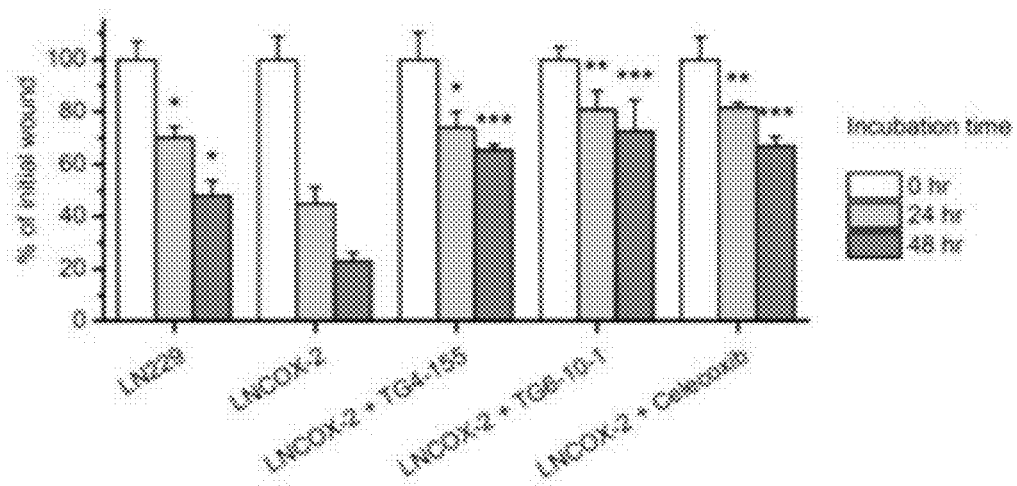
FIG. 3. Bar graph showing that overexpression of COX-2 in GBM cells LN229 increased wound closure, which was attenuated by TG4-155 (10 µM), TG6-10-1 (10 µM), and celecoxib (10 µM).

This Example demonstrates that in vitro inhibition of $PGE_2$ receptor EP2 by selective small-molecule antagonists TG4-155, TG6-10-1, or COX-2 selective inhibitor celecoxib suppressed the invasion (FIG. 2) and migration (FIG. 3) of human malignant glioma cells that are associated with COX-2 activation. The EP2 receptor mediates COX-2 activation-promoted glioma cell invasion. Overexpression of COX-2 in human GBM cells SF767 increased cell invasion, which was attenuated by EP2 antagonists—TG4-155 (10 µM), TG6-10-1 (10 µM), or COX-2 inhibitor celecoxib (10 µM), measured after 48 h (n=4, **P<0.01 compared with control group, one-way ANOVA and post-hoc Dunnett's test). Data are shown as mean+SEM.

PGE2 signaling via the EP2 receptor facilitates wound healing in human GBM cells. The data shows that overexpression of COX-2 in GBM cells LN229 increased wound closure, which was attenuated by TG4-155 (10 µM), TG6-10-1 (10 µM), and celecoxib (10 µM) (n=3, *P<0.05; P<0.01; *P<0.001 compared with COX-2 overexpression group, two-way ANOVA). Data are shown as mean+SEM.

Example 3

Figure 4:
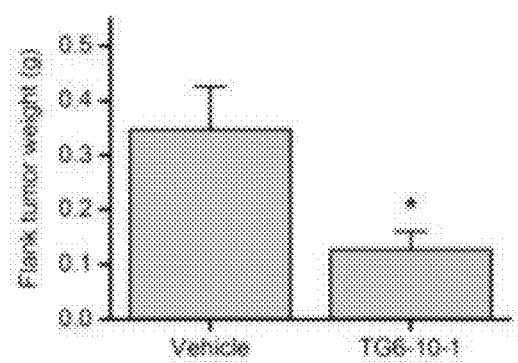
FIG. 4. Bar graph comparing flank tumor size in athymic nude mice treated with vehicle versus mice treated with TG6-10-1 measured 4 weeks after xenograft surgery.

This Example demonstrates that post-treatment with TC6-10-1 (FIG. 7) reduced the growth of subcutaneous tumors formed by human malignant glioma cells in mice (FIG. 4). Pharmacological inhibition of EP2 receptor by compound TG6-10-1 (10 mg/kg, p.o., b.i.d.) reduced the growth of flank tumors formed by human GBM cells SF767 in athymic nude mice, measured 4 weeks after xenograft surgery (n=7, *P<0.05, t-test). Data are shown as mean+SEM.

Example 4

Figure 5:
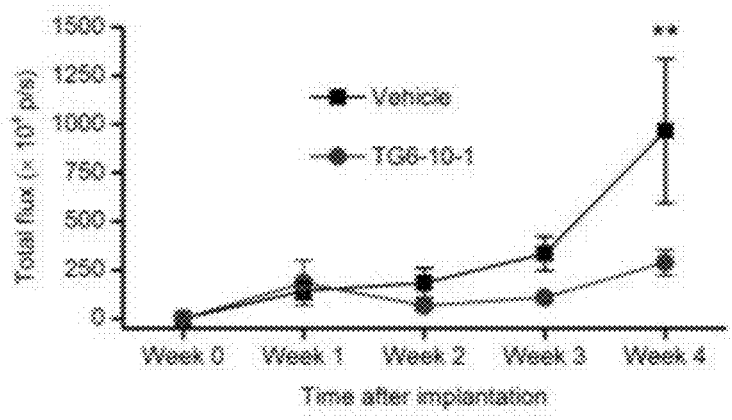
FIG. 5. Graph showing pharmacological inhibition of EP2 receptor by compound TG6-10-1 reduced the growth of intracranial tumors formed by human GBM cells LN229 in athymic nude mice, measured by bioluminescence weekly.
Figure 8:
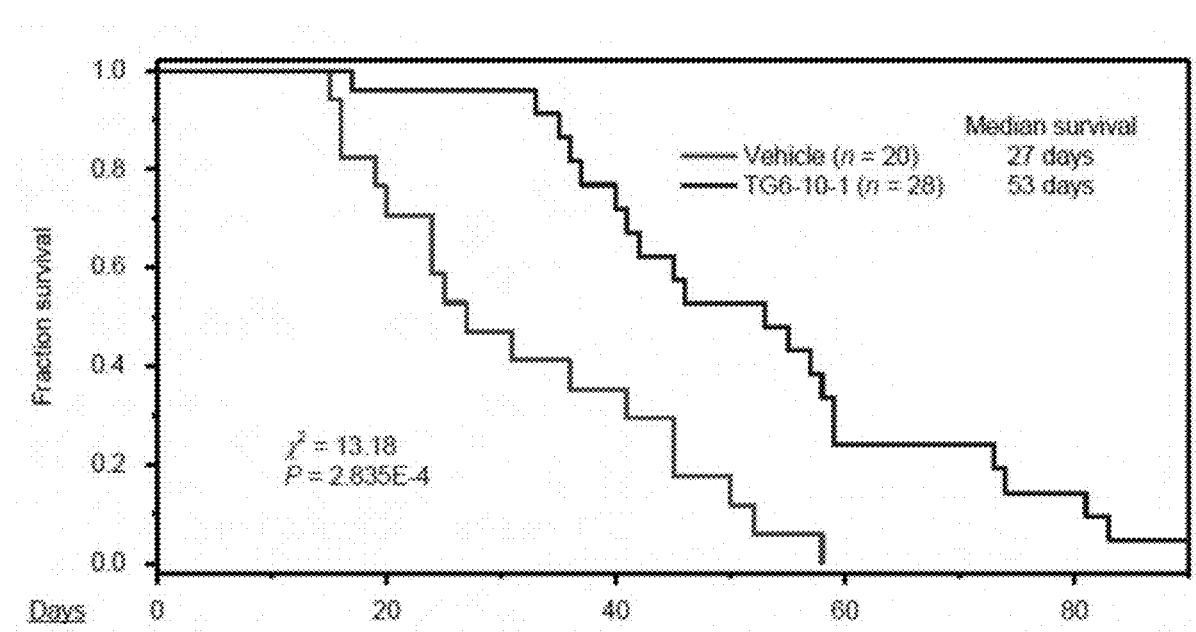
FIG. 8. Graph showing that the survival rate of mice harboring intracranial tumors derived from human GBM cells LN229 receiving TG6-10-1 is greater than the survival rate of mice receiving vehicle only.

Furthermore, TG6-10-1 treatment also suppressed the development of orthotopic brain tumors formed by these glioma cells in mice (FIG. 5), accompanied by improved survival (FIG. 8).

Pharmacological inhibition of EP2 receptor by compound TG6-10-1 (10 mg/kg, p.o., b.i.d.) reduced the growth of intracranial tumors formed by human GBM cells LN229 in athymic nude mice, measured by bioluminescence weekly (n=7, **P<0.01, two-way ANOVA). Data are shown as mean±SEM.

Survival rates of mice that harbored intracranial tumors derived from human GBM cells LN229 after receiving vehicle (n=20) or TG6-10-1 (n=28) for 28 days (P=2.835E-4 Kaplan-Meier survival analysis with post-hoc log-rank test).

Those skilled in the art will recognize, or be able to ascertain using no more than routine experimentation, many equivalents to the specific embodiments of the invention described herein. The scope of the present invention is not intended to be limited to the above Description and Examples, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given composition or method. The invention also includes embodiments in which more than one, or all group members are present in, employed in, or otherwise relevant to a given composition or method. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of using the composition for any of the purposes disclosed herein are included within the scope of the invention, and methods of making the composition according to any of the methods of making disclosed herein are included within the scope of the invention, unless otherwise indicated or unless it would be evident to one of ordinary skill in the art that a contradiction or inconsistency would arise. It should also be understood that, in general, where the invention, or embodiments and aspects of the invention, is/are referred to as comprising particular elements, features, etc., certain embodiments of the invention or aspects of the invention consist, or consist essentially of, such elements, features, etc. "Consist essentially" in accordance with the disclosure means that in addition to the recited element(s), non-essential elements may or may not be present.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any particular embodiment, aspect, element, feature, etc., of the present invention, or any combination thereof, may be explicitly excluded from any one or more claims whether or not such exclusion is expressly recited herein.

What is claimed:

1. A method of treating a subject suffering from malignant glioma, the method comprising administering to the subject a pharmaceutical composition comprising a selective EP2 antagonist selected from the group consisting of TG4-155, TG6-10-1, and combinations thereof, whereby invasion and/or migration of glioma cells is suppressed, thereby treating the subject.

2. The method according to claim 1, wherein the subject suffers from glioma selected from grade II-IV astrocytoma, oligodendroglioma and oligoastrocytoma.

3. The method according to claim 2, wherein the glioma is a grade IV astrocytoma selected from primary and secondary glioblastoma (GB).

4. The method according to claim 1, wherein the subject is human or non-human animal.

5. The method according to claim 1, wherein the selective EP2 antagonist TG4-155 is defined by the following structure:

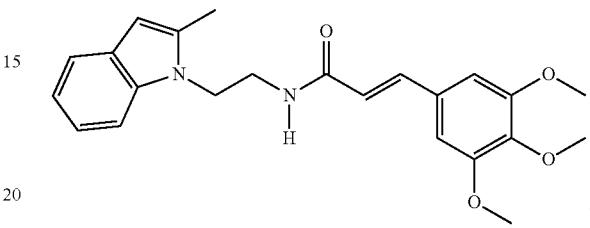

6. The method according to claim 1, wherein the selective EP2 antagonist TG6-10-1 is defined by the following structure:

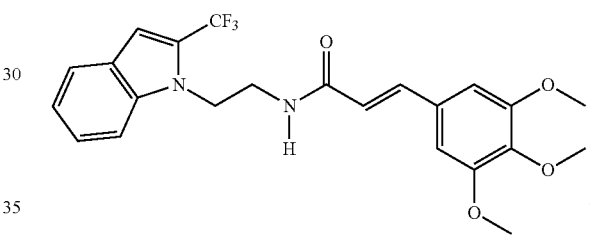

7. The method according to claim 1 wherein administering comprises via oral, rectal, subcutaneous, intravenous, intramuscular, intranasal or infusive routes.

8. The method according to claim 1 wherein administering comprises administering a dose of between 0.01 and 1000 mg/kg, between 0.1 and 500 mg/kg, between 1 and 250 mg/kg body weight, or 5, 10, 20, 50, 100, 150, 200 or 250 mg/kg body weight of the subject per day in one or multiple doses.

* * * * *